United States Patent [19]

Fouquet et al.

[11] 4,118,588

[45] Oct. 3, 1978

[54] MANUFACTURE OF METHACRYLIC ACID AND METHYL METHACRYLATE

[75] Inventors: Gerd Fouquet, Ludwigshafen; Franz Merger, Frankenthal; Rolf Platz, Mannheim; Karl Baer, Weinheim, all of Fed. Rep. of Germany

[73] Assignee: BASF Aktiengesellschaft, Ludwigshafen, Fed. Rep. of Germany

[21] Appl. No.: 781,149

[22] Filed: Mar. 25, 1977

[30] Foreign Application Priority Data

Apr. 10, 1976 [DE] Fed. Rep. of Germany ....... 2615887
Feb. 12, 1977 [DE] Fed. Rep. of Germany ....... 2706076

[51] Int. Cl.$^2$ ............................................. C07C 69/52
[52] U.S. Cl. .................... 560/210; 560/211; 562/599
[58] Field of Search ................... 260/526 R; 560/211, 560/210

[56] References Cited

U.S. PATENT DOCUMENTS 3,014,958  12/1961  Koch et al. ........................... 260/486

FOREIGN PATENT DOCUMENTS 2,457,993  6/1976  Fed. Rep. of Germany.
1,428,277  8/1972  United Kingdom.
1,447,669  9/1973  United Kingdom.

Primary Examiner—James O. Thomas, Jr.
Assistant Examiner—L. Hendriksen
Attorney, Agent, or Firm—Keil, Thompson & Shurtleff

[57] ABSTRACT

Methacrylic acid and methyl methacrylate are manufactured by reacting, respectively, propionic acid and methyl propionate with dimethoxymethane in the presence of catalysts based on phosphates and/or silicates of magnesium, calcium, aluminum, zirconium, thorium and/or titanium, and in the presence of from 0 to 0.5 mole of water per mole of the acetal.

12 Claims, No Drawings

MANUFACTURE OF METHACRYLIC ACID AND METHYL METHACRYLATE

The present invention relates to a new process for the manufacture of methacrylic acid and methyl methacrylate by reacting, respectively, propionic acid and methyl propionate with dimethoxymethane in the presence of catalysts based on aluminum, magnesium, calcium, zirconium, thorium and/or titanium, in the presence or absence of boric acid and/or urea, using short residence times.

U.S. Pat. No. 3,014,958 discloses reacting formaldehyde in aqueous solution with methyl propionate, in the molar ratio of from 1:1.5 to 1:20, over dehydration catalysts at from 225° to 450° C., in the presence of not less than 7 percent by weight of methyl methacrylate. The best yield of methyl methacrylate, based on formaldehyde employed, is 84%, when employing a molar ratio of methyl propionate:formaldehyde:water:methyl methacrylate of 10:1:1:0.8 and using a mixture of $K_2O$, MgO and $Fe_2O_3$ as the catalyst. If calcium phosphate is used, the yield is only 43% of less, whilst in the case of aluminum phosphate it is 46%.

British Patent 1,428,277 discloses the manufacture of methyl methacrylate from an alkyl propionate, formaldehyde and water, in the presence or absence of methanol, and in the presence of a compound of main group 1 of the periodic table, on a carrier, as a catalyst having a specific surface area of from 350 to 1,000 $m^2.g^{-1}$, the reaction being carried out at from 400° to 600° C., and a molar ratio of water:formaldehyde of from 0.01:1 to 10:1 being required. In the Examples, an inert gas is introduced in order to dilute the reaction mixture. In one Example (Example 1) which gives a good space-time yield compared to the other Examples, yields of methyl methacrylate of up to 92% are achieved, with 67% conversion of formaldehyde, when using a ratio of methyl propionate:formaldehyde:water:methanol of 4.5:1:5.3:6.7. Preferred carriers are silica gels and siliceous earths having the above structure. The only catalysts described in the Examples are potassium hydroxide and rubidium carbonate on silica gel. Water is an essential starting material; without it, virtually no condensation to give methyl methacrylate occurs (Example 4). Very good yields are only achievable with catalysts having a large surface area, produced by special methods (Example 11).

British Pat. No. 1,447,669 discloses the reaction of formaldehyde with an alkanoic acid or its ester in the presence of basic catalysts containing pyrogenic silica; catalysts containing an alkali metal hydroxide are preferred. A molar ratio of alkanoic acid:formaldehyde:-water:methanol of from 1:1:0.01:0 to 1:1:6:0.03 is disclosed. With a molar ratio of propionic acid:formaldehyde:water:methanol of 20:20:59:1 and a maximum of 34% conversion of formaldehyde and propionic acid to methacrylic acid and methyl methacrylate, yields of from 58 to 69%, based on formaldehyde converted, or of from 58 to 80%, based on propionic acid converted, are achieved; when reacting methyl propionate with formaldehyde, water and methanol in the same molar ratio, yields of 63% and 44%, respectively, are obtained, for 25% conversion; potassium hydroxide on pyrogenic silica is used as the catalyst.

We have found that methacrylic acid and methyl methacrylate, i.e. methacrylic compounds, of the formula

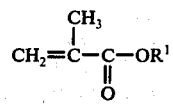

where $R^1$ is hydrogen or methyl, i.e. is a substituent chosen from H and $CH_3$, are obtained in an advantageous manner if propionic acid or methyl propionate, i.e. a carboxyl compound of the formula

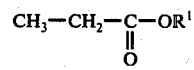

where $R^1$ has the above meanings, is reacted with dimethoxymethane of the formula

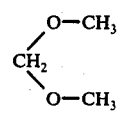

in the presence of catalysts based on one or more salts selected from phosphates and silicates of magnesium, calcium, aluminum, zirconium, thorium and titanium, the reaction time being from 0.1 to 100 seconds and the reaction being carried out in the presence of from 0 to 0.5 mole of water per mole of starting material III. The catalysts may be used by themselves or together with oxides of magnesium, calcium, zirconium, aluminum, thorium and/or titanium and/or with boric acid and/or with urea.

If dimethoxymethane and methyl propionate, which is a preferred compound II, are used, the reaction can be represented by the following equation:

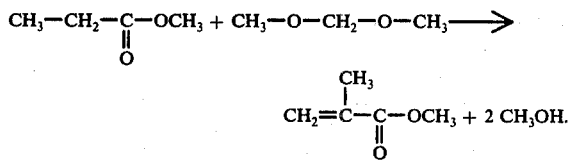

Compared to the conventional processes, the process of the invention gives methacrylic acid and/or methyl methacrylate more simply and more economically, in good yield and high purity. Surprisingly, in spite of the formaldehyde being blocked in the form of the dimethylacetal (not previously known as a starting material), reaction with propionic acid or methyl propionate to give the methacrylic compound I occurs. It was not to be expected from the prior art that the reaction could be carried out even with very small amounts of water or — with even higher yields — in the absence of water, this being the common embodiment of the process of the invention. It is particularly surprising that the starting materials of the invention can be condensed, with good space-time yield and good selectivity, even in the temperature range below the optimum temperature for the condensation with formaldehyde by conventional processes. Since water is in general neither deliberately introduced nor produced by the reaction according to the invention, hydrolysis of the esters is avoided and accordingly it is not necessary to use any methanol as a starting material. The process saves energy and materials. Further advantages are that the reaction mixture can be worked up more easily and in an energy-saving manner, and that any unconverted formaldehyde can be recycled, in the form of the dimethylacetal, more simply than hitherto, thus facilitating purification of the effluent. The process of the invention causes particularly little pollution of the environment. A further advantage is that additional diluents, eg. solvents or inert gases, which, when used, make condensing and distilling of the reaction mixtures more difficult, are dispensed with; the losses of end product entailed in removing the diluent are also avoided. For the same degree of conversion and the same yield, based on dimethoxymethane, it is possible, surprisingly, to dispense with the use of special catalysts, of large specific surface area, which are expensive to manufacture, and to dispense with the use of methyl methacrylate in the starting mixture. Accordingly, high conversions and selectivities are achieved even with catalysts of which the manufacture, performance in sustained use and regeneration present comparatively few problems.

The starting material II and III are employed in stoichiometric amounts or in excess of either one over the other, advantageously in a ratio of from 0.01 to 20, preferably from 1 to 10, especially from 2 to 6, moles of starting material II per mole of starting material III.

The reaction is in general carried out at from 200° to 500° C., preferably from 250° to 450° C., especially from 270° to 400° C., under atmospheric or superatmospheric pressure, continuously or batchwise, in a fixed bed or a fluidized catalyst bed. Preferably, the reaction is carried out without added solvents and in particular without added water. If appropriate, from 0 to 0.5, for example from 0.01 to 0.1, mole of water may be used per mole of acetal (starting material III). Suitable reaction times, or residence times of the starting mixture in the reaction chamber, are in general from 0.1 to 100, preferably from 0.2 to 50, especially from 0.5 to 40, seconds.

The catalysts used are phosphates and/or silicates of magnesium, calcium, aluminum, zirconium, thorium and/or titanium, by themselves or together with oxides of magnesium, calcium, zirconium, aluminum, thorium and/or titanium and/or boric acid and/or urea. Amongst the metals mentioned, aluminum, titanium and zirconium are more advantageous than magnesium, calcium and thorium; as to the type of compounds, phosphates are more advantageous than silicates and both groups of compounds are more advantageous than oxides. A combination of the metal compounds with boric acid and/or urea is particularly advantageous.

The preferred catalysts, in sequence of decreasing preference, are: (1) aluminum phosphate, titanium dioxide, boric acid and urea; (2) aluminum phosphae, zirconium dioxide, boric acid and urea; (3) aluminum phosphate, or aluminum phosphate and titanium dioxide; (4) aluminum phosphate, zirconium dioxide and boric acid; (5) aluminum phosphate, thorium dioxide, boric acid and urea; (6) aluminum phosphate, aluminum oxide, boric acid and urea; (7) aluminum phosphate, titanium dioxide and urea; (8) aluminum phosphate, thorium dioxide and boric acid; (9) aluminum phosphate, aluminum oxide and boric acid; (10) aluminum phosphate, aluminum oxide and urea; (11) aluminum phosphate, urea and boric acid; (12) aluminum phosphate and boric acid; (13) aluminum phosphate and urea; (14) aluminum phosphate and aluminum oxide; (15) aluminum phosphate and magnesium silicate; (16) aluminum phosphate, aluminum silicate, boric acid and urea; (17) aluminum phosphate, aluminum silicate and boric acid; (18) aluminum phosphate, aluminum silicate and urea; (19) aluminum phosphate and aluminum silicate; (20) aluminum phosphate and magnesium phosphate; (21) aluminum oxide, titanium dioxide, boric acid and urea; (22) aluminum oxide, titanium dioxide and boric acid; (23) aluminum oxide, titanium dioxide and urea; (24) aluminum oxide and titanium dioxide; (25) aluminum oxide, boric acid and urea; (26) aluminum oxide and boric acid; (27) aluminum oxide and urea; (28) titanium dioxide, boric acid and urea; (29) titanium dioxide and boric acid; (30) titanium dioxide, calcium phosphate, boric acid and urea; (31) titanium dioxide, calcium phosphate and boric acid; (32) titanium dioxide, calcium phosphate and urea; (33) titanium dioxide, magnesium silicate, boric acid and urea; (34) titanium dioxide, magnesium silicate and boric acid; (35) titanium dioxide, magnesium silicate and urea; (36) titanium dioxide, thorium phosphate, boric acid and urea; (37) titanium dioxide, thorium phosphate and boric acid; (38) titanium dioxide, thorium phosphate and urea; (39) titanium dioxide and thorium dioxide; (40) titanium dioxide and thorium phosphate; (41) titanium dioxide, zirconium dioxide; boric acid and urea; (42) zirconium phosphate, boric acid and urea; (43) zirconium dioxide, calcium phosphate, boric acid and urea; (44) aluminum phosphate, calcium phosphate, boric acid and urea; (45) aluminum phosphate, calcium phosphate and boric acid; (46) aluminum phosphate and calcium phosphate; (47) calcium phosphate, boric acid and urea; (48) calcium phosphate and boric acid; (49) calcium phosphate and urea; (50) calcium phosphate and aluminum phosphate; (51) calcium phosphate, titanium dioxide, zirconium dioxide, boric acid and urea; (52) calcium phosphate; (53) zirconium dioxide and boric acid; (54) zirconium dioxide, boric acid and urea; (55) thorium dioxide, boric acid and urea; (56) magnesium silicate, boric acid and urea; (57) magnesium silicate and boric acid; (58) magnesium silicate and urea; (59) magnesium silicate, aluminum silicate, boric acid and urea; (60) aluminum silicate, titanium dioxide, boric acid and urea; (61) aluminum silicate, titanium dioxide and boric acid and (62) aluminum silicate.

Each catalyst or each catalyst combination in the above sequence constitutes, together with all the previously mentioned catalysts in the sequence, a particularly preferred selected group compared to the remaining, subsequently mentioned catalysts of the series. Thus, aluminum phosphate, boric acid/urea/titanium dioxide is a selected preferred group compared to aluminum phosphate, boric acid/urea/zirconium dioxide and all remaining catalysts; aluminum phosphate, boric acid/urea/titanium dioxide is, in turn, a selected, preferred group compared to magnesium silicate and all remaining catalysts of the series.

The reaction according to the invention is carried out particularly advantageously in the presence of catalysts which are modified with alkali metal carboxylates and/or alkaline earth metal carboxylates and/or alkali metal compounds and/or alkaline earth metal compounds which form carboxylates under the reaction conditions. This modification greatly improves the space-time yield of the catalysts in the reaction of II with III.

Suitable modifiers of this type are, above all, the carboxylates, oxides and hydroxides of lithium, sodium, potassium, magnesium and calcium, as well as of rubidium, cesium, beryllium, strontium and barium, and also alkali metal and/or alkaline earth metal silicates, borates, carbonates, bicarbonates and/or alcoholates.

Suitable carboxylates are, above all, those derived from aliphatic carboxylic acids of 1 to 10 carbon atoms, eg. the formates, acetates, propionates and butyrates of lithium, sodium, potassium, magnesium and calcium, the acrylates and methacrylates of lithium, potassium, sodium, magnesium and calcium, and the 2-ethylhexanoates, succinates, maleates and oxalates of lithium, potassium and calcium. Carboxylates of the said type, which are of 3 to 4 carbon atoms and are derived from lithium and/or potassium, above all lithium propionate, lithium methacrylate, potassium propionate, potassium methacrylate, lithium fumarate and potassium maleate, are of particular interest. The preferred carboxylates are the propionates of the alkali metals, especially lithium propionate and potassium propionate. The preferred alkali metal compounds and alkaline earth metal compounds which form carboxylates under the reaction conditions are lithium hydroxide and potassium hydroxide.

Other examples of suitable modifiers are calcium oxide and magnesium oxide, potassium magnesium silicate, calcium borate, potassium bicarbonate, lithium carbonate, sodium carbonate, sodium silicate, magnesium bicarbonate, sodium methylate, calcium ethylate and potassium propanolate.

The amount of modifier may be varied within wide limits and is in most cases from 0.05 to 30, especially from 0.1 to 25, % by weight of alkali metal and/or alkaline earth metal, or of the ions of these metals, based on modified catalyst (excluding carriers). Catalysts based on phosphates of aluminum, titanium, zirconium and/or thorium, which are preferred, may advantageously be modified with from 0.1 to 15, especially from 0.2 to 10, % by weight of alkali metal and/or alkaline earth metal, based on the modified catalyst, in the form of carboxylates of carboxylic acids of 3 to 4 carbon atoms, especially propionates and/or methacrylates, and/or of hydroxides, of the alkali metals and/or alkaline earth metals, preferably of lithium and potassium; phosphate of aluminum, modified with from 0.3 to 8% by weight of lithium and/or potassium, based on modified catalyst, in the form of propionates and/or hydroxides, have proved particularly advantageous.

The modified catalysts can be manufactured from the principal constituents, for example aluminum phosphates, and the modifiers by, for example, heating in the presence of water, evaporating off the water and drying at an elevated temperature. Another advantageous method is to work the principal constituents, together with the modifiers, into a paste by adding small amounts of water, homogenize the paste by kneading and extrude it to form strands, comminute the latter and then evaporate off the water, at elevated temperatures, from the nibs obtained. Very suitable modified catalysts are also obtained by producing the principal constituents, for example the phosphates of aluminum, thorium, titanium and/or zirconium, by precipitation in the presence of modifiers, for example carboxylates and/or hydroxides and/or nitrates of lithium and/or potassium, through adding phosphoric acid, with or without ammonia, to aqueous solutions of the nitrates of the metals of which the phosphates are required. Aqueous solutions of ammonium phosphates, which contain potassium phosphates, may also be used as precipitants for the manufacture of aluminum phosphates modified with potassium ions. The precipitated phosphates, e.g. of aluminum, containing co-precipitated modifier, can, after isolation from the aqueous phase, be dried at an elevated temperature, advantageously at from 100° to 200° C., if appropriate whilst passing hot air over the material.

Finally, the modified catalysts can also be manufactured by starting from aqueous aluminate solutions, from which the phosphates are precipitated by mixing with phosphoric acid, with or without the addition of aqueous solutions of nitrates of aluminum, zirconium and/or titanium. The phosphoric acid can advantageously be employed in slight excess; its preferred concentration is from 10 to 80% by weight, preferably from 20 to 60% by weight. In the case of co-precipitation of the phosphates and the modifiers, the aqueous reaction mixture is advantageously at from 20° to 90° C., preferably from 40° to 70° C. It is furthermore advantageous if, when co-precipitating phosphates and modifiers, the aqueous phase is brought to a pH of from 7 to 10, especially of from 8 to 9, before it is separated off.

After drying, the modified catalysts can be calcined, for example by heating at from 300° to 600° C., especially from 400° to 500° C., for from 1 to 10 hours, especially from 2 to 5 hours.

The modified catalysts are particularly selective for the reaction of II with III and particularly small amounts of by-products, eg. methyl isobutyrate (produced in a yield of less than 0.5 mole %) are obtained. In addition, the reaction mixture is particularly simple to work up.

In continuous operation, it is advantageous to use from 2 to 2,500, preferably from 5 to 1,500, and especially from 5 to 500, kilograms of combination of starting materials II and III per kilogram of catalyst per hour. In the case of mixed catalysts, it is advantageous to use a ratio of from 5 to 50, preferably from 8 to 40, percent by weight of boric acid or from 1 to 20, preferably from 2 to 15, percent by weight of urea, based on metal compound, or from 6 to 70, preferably from 10 to 55, percent by weight of boric acid and urea taken together, based on metal compound, or from 250 to 500, preferably from 270 to 400, percent by weight of boric acid, based on urea. The components, eg. the oxides, phosphates and silicates, may be present in the catalysts as components of a mixture or of a crystal lattice, or in the form of mixed crystals. If higher temperatures, eg. above 400° C., are used for the manufacture of the catalyst, or for the reaction, a greater or lesser proportion of the urea — depending on the temperature — may be converted to secondary products thereof, without any substantial adverse effect on the activity of the catalyst.

The reaction may be carried out as follows: a mixture of starting material II and starting material III, in the gas phase or vapor phase, is passed over the catalyst at the reaction temperature for the stated reaction time. The end product is then isolated from the reaction mixture in the conventional manner, for example by cooling and fractional distillation.

Methacrylic acid and methyl methacrylate, obtainable by the process of the invention, are well-known as valuable starting materials for the manufacture of plastics, finishing agents, adhesives, lubricating oil additives and crop protection agents. For details of their use, reference may be made to the publications cited above and to Ullmanns Encyklopadie der technischen Chemie, volume 12, pages 392–396.

In the Examples which follow, parts are by weight.

EXAMPLE 1

130 parts of aluminum phosphate (4 mm extrudates), having a composition corresponding to 42 percent by weight of $Al_2O_3$ and 58 percent by weight of $P_2O_5$, are introduced into a tubular reactor equipped with a vaporizer. The reaction is heated to 300° C. and a mixture of 3.8 parts of dimethoxymethane and 44 parts of methyl propionate is passed through it in the course of 60 minutes. The residence time is 27.8 seconds. The reaction mixture is analyzed by gas chromatography and subjected to fractional distillation. The conversion to methyl methacrylate is 83%, based on dimethoxymethane and the yield (based on analysis) is 4.2 parts (84% of theory, spaced-time yield 21 g/liter of reactor volume/hour) of methyl methacrylate.

EXAMPLE 2

The reaction is carried out as described in Example 1. The reactor is charged with 88 parts of methyl propionate and 7.6 parts of dimethoxymethane in the course of 30 minutes at 350° C. The residence time is 6.4 seconds. The reaction mixture is analyzed by gas chromatography and subjected to fractional distillation. The conversion to methyl methacrylate is 79%, based on dimethoxymethane and the yield (based on analysis) is 7.9 parts (81% of theory, space-time yield 79 g/liter/hour) of methyl methacrylate.

EXAMPLE 3

(a) Manufacture of the catalyst: 300 parts of titanium dioxide (anatase), 230 parts of calcium phosphate and 75 parts of boric acid are mixed in a kneader. A solution of 25 parts of urea in 50 parts of water is then added and a paste is produced. The paste is dried for 12 hours at 120° C. and is then heated for 3 hours at 580° C. The mixture is then milled and sieved.

(b) 125 parts of catalyst (particle size from 0.5 to 1 mm are introduced into a reactor and the latter is heated at 400° C. and charged with 88 parts of methyl propionate and 15.2 parts of dimethoxymethane in the course of 30 minutes. The residence time is 5.9 seconds. The reaction mixture is analyzed by gas chromatography and subjected to fractional distillation. The conversion to methyl methacrylate is 38%, based on dimethoxymethane and the yield (based on analysis) is 6.1 parts (46% of theory) of methyl methacrylate.

EXAMPLE 4

(a) Manufacture of the catalyst: 300 parts of titanium dioxide (anatase), 230 parts of aluminum phosphate and 75 parts of boric acid are mixed in a kneader. A solution of 25 parts of urea in 50 parts of water is then added and a paste is produced. The paste is dried for 2 hours at 120° C. and is then heated for 3 hours at 600° C. The catalyst mass is then milled and sieved.

(b) 130 parts of catalyst (particle size from 0.5 to 1 mm) are introduced into a reactor and heated at 350° C. 88 parts of methyl propionate and 7.6 parts of dimethoxymethane are passed over the catalyst in the course of 30 minutes. The residence time is 6.4 seconds. The reaction mixture is analyzed by gas chromatography and subjected to fractional distillation. The conversion to methyl methacrylate is 92%, based on dimethoxymethane and the yield (based on analysis) is 9.2 parts (95% of theory, space-time yield 92 g/liter of reactor volume/hour) of methyl methacrylate.

EXAMPLE 5

A catalyst is manufactured, by the method described in Example 4a, from 300 parts of zirconium dioxide, 230 parts of aluminum phosphate, 75 parts of boric acid and 25 parts of urea. 120 parts of this catalyst (particle size from 0.5 to 1 mm) are introduced into a reactor and the latter is heated at 300° C. and charged with 88 parts of methyl propionate and 7.6 parts of dimethoxymethane in the course of 30 minutes. The residence time is 7 seconds. The reaction mixture is analyzed by gas chromatography and subjected to fractional distillation. The conversion to methyl methacrylate is 88%, based on dimethoxymethane and the yield (based on analysis) is 8.8 parts (89% of theory, space-time yield 88 g/liter of reactor volume/hour) of methyl methacrylate.

EXAMPLE 6

A catalyst is manufactured, by the method described in Example 3a, from 300 parts of thorium dioxide, 230 parts of aluminum phosphate, 100 parts of boric acid and 35 parts of urea. 140 parts of this catalyst are introduced into a reactor and the latter is heated at 330° C. and charged with 176 parts of methyl propionate and 15.2 parts of dimethoxymethane in the course of 60 minutes. The residence time is 5.6 seconds. The reaction mixture is analyzed by gas chromatography and subjected to fractional distillation. The conversion to methyl methacrylate is 80%, based on dimethoxymethane and the yield (based on analysis) is 16 parts (85% of theory, space-time yield 80 g/liter of reactor volume/hour) of boiling point 100° C.

EXAMPLE 7

A catalyst is manufactured, by the method described in Example 3a, from 230 parts of aluminum phosphate, 75 parts of boric acid and 25 parts of urea. 130 parts of this catalyst are introduced into a reactor and the latter is heated at 400° C. and charged with a mixture of 7.6 parts of dimethoxymethane and 88 parts of methyl propionate in the course of 30 minutes. The residence time is 5.9 seconds. The reaction mixture is analyzed by gas chromatography and subjected to fractional distillation. The conversion to methyl methacrylate is 76%, based on dimethoxymethane and the yield (based on analysis) is 7.6 parts (80% of theory, space-time yield 76 g/liter of reactor volume/hour) of methyl methacrylate.

EXAMPLES 8 TO 10

| Example No. | Catalyst | Temperature ° C | Residence time in seconds | Conversion % | Yield % of theory |
|---|---|---|---|---|---|
| 8 | $AlPO_4$, $H_3BO_3$ +) | 380 | 6.1 | 62 | 65 |
| 9 | $AlPO_4$, $ThO_2$, $H_3BO_3$ ++) | 400 | 5.9 | 66 | 69 |
| 10 | Aluminum silicate | 400 | 5.9 | 15 | 25 |

-continued
EXAMPLES 8 TO 10

| Example No. | Catalyst | Temperature °C | Residence time in seconds | Conversion % | Yield % of theory |
|---|---|---|---|---|---|
| | (45% of $Al_2O_3$ + 55% of $SiO_2$) | | | | |

The reaction is carried out by the method described in Example 2.
The catalysts are manufactured by the method described in Example 3a.
+)(from 230 parts of $AlPO_4$ and 75 parts of $H_3BO_3$)
++)(from 230 parts of $AlPO_4$, 300 parts of $ThO_2$ and 75 parts of $H_3Bo_3$)

EXAMPLE 11

(a) Manufacture of the catalyst (analysis: 42% by weight of $Al_2O_3$, 58% by weight of $P_2O_5$, particle size from 3 to 4 mm). 100 parts by weight of aluminum phosphate, 20 parts of potassium propionate and 200 parts of water are boiled under reflux for 2 hours. The water is then evaporated off, after which the product is dried and calcined for 4 hours at 450° C.

(b) 50 parts of the catalyst obtained are introduced into a tubular reactor provided with a vaporizer. The catalyst is heated at 330° C. and is charged with 88 parts of methyl propionate and 7.6 parts of dimethoxymethane in the course of 30 minutes. The residence time of the reaction mixture over the catalyst is 3.3 seconds. The reaction mixture is subjected to fractional distillation and 8.8 parts (89% of theory, based on dimethoxymethane, space-time yield 176 g/liter of reactor volume/hour) of methyl methacrylate boiling at 100° C. are obtained.

EXAMPLE 12

Following the method described in Example 1 (a), a catalyst is manufactured from 100 parts of aluminum phosphate (as in Example 1), 7 parts of lithium hydroxide and 200 parts of water. 50 parts of the catalyst are introduced into the reactor (compare Example 1) and heated at 350° C. A mixture of 88 parts methyl propionate and 7.6 parts of dimethoxymethane is then passed over the catalyst in the course of 30 minutes, the residence time being 3.2 seconds. The reaction mixture is subjected to fractional distillation and 9.4 parts (97% of theory, based on dimethoxymethane, space-time yield 188 g/liter of reactor volume/hour) of methyl methacrylate, boiling at 100° C., are obtained.

EXAMPLE 13

Following the method described in Example 1 (a), a catalyst is manufactured from 100 parts of aluminum phosphate, 22 parts of potassium silicate ($K_2Si_4O_9$) and 200 parts of water. 60 parts of the catalyst are introduced into the reactor (compare Example 1) and heated at 350° C. A mixture of 88 parts of methyl propionate and 7.6 parts of dimethoxymethane is then passed over the catalyst in the course of 30 minutes, the residence time being 3.2 seconds. The reaction mixture is subjected to fractional distillation and 5.2 parts (54% of theory, based on dimethoxymethane, space-time yield 104 g/liter of reactor volume/hour) of methyl methacrylate, boiling at 100° C, are obtained.

EXAMPLE 14

Following the method described in Example 1 (a), a catalyst is manufactured from 100 parts of aluminum phosphate, 10 parts of barium hydroxide and 200 parts of water. 60 parts of the catalyst are introduced into the reactor (compare Example 1) and heated at 350° C. A mixture of 88 parts of methyl propionate and 7.6 parts of dimethoxymethan is then passed over the catalyst in the course of 30 minutes, the residence time being 3.2 seconds. The reaction mixture is subjected to fractinal distillation and 5.0 parts (52% of theory, based on dimethoxymethane, space-time yield 100 g/liter of reactor volume/hour) of methyl methacrylate, boiling at 100° C, are obtained.

EXAMPLE 15

Following the method described in Example 1 (a), a catalyst is manufactured from 100 parts of zirconium phosphate, 151 parts of potassium propionate and 200 parts of water. 60 parts of the catalyst are introduced into the reactor (compare Example 1) and heated at 360° C. A mixture of 88 parts of methyl propionate and 7.6 parts of dimethoxymethane is then passed over the catalyst in the course of 45 minutes, the residence time being 4.8 seconds. The reaction mixture is subjected to fractional distillation and 7.5 parts (79% of theory, based on dimethoxymethane, space-time yield 100 g/liter of reactor volume/hour) of methyl methacrylate, boiling at 100° C, are obtained.

We claim:

1. A process for the manufacture of methacrylic compounds of the formula

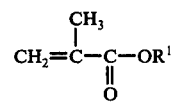

where $R^1$ is a substituent chosen from H and $CH_3$ which comprises reacting a carboxyl compound of the formula

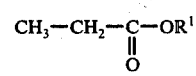

where $R^1$ has the above meaning, with dimethoxymethane of the formula

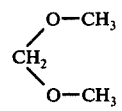

in the presence of catalysts containing one or more salts selected from the group consisting of phosphates and silicates of magnesium, calcium, aluminum, zirconium, thorium and titanium, the reaction time being from 0.1 to 100 seconds and the reaction being carried out in the presence of from 0 to 0.5 mole of water per mole of starting material III.

2. A process for the manufacture of methacrylic compounds as set forth in claim 1, wherein the reaction is carried out in the presence of catalysts which in addition contain at least one oxygen compound slected from the group consisting of oxides of magnesium, calcium, aluminu, zirconium, thorium and titanium.

3. A process for the manufacture of methacrylic compounds as set forth in claim 1, wherein the reaction is carried out in the presence of catalysts which additionally contain boric acid.

4. A process for the manufacture of methacrylic compounds as set forth in claim 1, wherein the reaction is carried out in the presence of catalysts which additionally contain urea.

5. A process for the manufacture of methacrylic compounds as set forth in claim 1, wherein the reaction is carried out in the presence of catalysts which are modified with salts chosen from carboxylates of the alkali metals and alkaline earth metals.

6. A process for the manufacture of methacrylic compounds as set forth in claim 1, wherein the reaction is carried out in the presence of catalysts which are modified with compounds chosen from alkali metal compounds and alkaline earth metal compounds which form carboxylates under the reaction conditions.

7. A process for the manufacture of methacrylic compounds as set forth in claim 1, wherein the reaction is carried out in the presence of catalysts which are modified with alkali metal propionates.

8. A process for the manufacture of methacrylic compounds as set forth in claim 1, wherein the reaction is carried out in the presence of catalysts which are modified with hydroxides chosen from postassium hydroxide and lithium hydroxide.

9. A process for the manufacture of methacrylic compounds as set forth in claim 1, wherein the reaction is carried out in the presence of catalysts chosen rom phosphates of aluminum, zirconium, thorium and titanium, modified with carboxylates of alkali metals and alkaline earth metals, the carboxyate groupseach being of 3 or 4 carbon atoms.

10. A process for the manufacture of methacrylic compounds as set forth in claim 1, wherein the reaction is carried out in the presence of catalysts based in aluminum phosphates modified with alkali metal propionates.

11. A process for the manufacture of methacrylic compounds as set forth in claim 1, wherein the reaction is carried out in the presence of catalysts based on aluminum phosphates modified with hydroxides chosen from lithium hydroxide and potassium hydroxide.

12. A process for the manufacture of methacrylic compounds as set forth in claim 1, wherein the reaction is carried out in the absence of water.

* * * * *